(12) United States Patent
Feibel et al.

(10) Patent No.: US 9,907,598 B2
(45) Date of Patent: Mar. 6, 2018

(54) DEVICE FOR TENSIONING APPARATUS FOR FUSION, STABILIZATION, AND/OR FIXATION OF BONES

(71) Applicants: Jonathan Feibel, Columbus, OH (US); Robert Gorsline, Columbus, OH (US)

(72) Inventors: Jonathan Feibel, Columbus, OH (US); Robert Gorsline, Columbus, OH (US); Nicholas Joseph Vallo, New Albany, OH (US); Christos Ragais, New Albany, OH (US); Christopher Brown, Columbus, OH (US); Christopher Hawker, Columbus, OH (US); Jeffrey J. Root, Columbus, OH (US)

(73) Assignees: Jonathan Feibel, Columbus, OH (US); Robert Gorsline, Columbus, OH (US)

( * ) Notice: Subject to any disclaimer, the term of this patent is extended or adjusted under 35 U.S.C. 154(b) by 388 days.

(21) Appl. No.: 14/562,616

(22) Filed: Dec. 5, 2014

(65) Prior Publication Data
US 2015/0157380 A1 Jun. 11, 2015

Related U.S. Application Data

(60) Provisional application No. 61/925,644, filed on Jan. 9, 2014, provisional application No. 61/912,540, filed on Dec. 5, 2013.

(51) Int. Cl.
*A61B 17/88* (2006.01)
*A61B 17/80* (2006.01)
(Continued)

(52) U.S. Cl.
CPC ...... *A61B 17/8869* (2013.01); *A61B 17/8019* (2013.01); *A61B 2017/681* (2013.01); *A61B 2090/064* (2016.02); *A61B 2090/065* (2016.02)

(58) Field of Classification Search
CPC .............................. A61B 17/88; A61B 17/8869
See application file for complete search history.

(56) References Cited

U.S. PATENT DOCUMENTS 5,788,697 A * 8/1998 Kilpela .............. A61B 17/8869
254/199
2008/0287951 A1 11/2008 Stoneburner et al.
(Continued)

FOREIGN PATENT DOCUMENTS

DE 8813344 U1 1/1989
EP 1192908 A2 4/2002

OTHER PUBLICATIONS

International Search Report related to International App. No. PCT/US2014/068952.
(Continued)

*Primary Examiner* — Christopher Beccia
(74) *Attorney, Agent, or Firm* — Benesch Friedlander Coplan & Aronoff LLP (57) ABSTRACT

Various embodiments of a device for tensioning an apparatus for fusion, stabilization, and/or fixation of bones are disclosed. In one embodiment, a device for tensioning an orthopedic device is provided, the device comprising: a screw drive; a screw gear; a body portion comprising a first cam lever and a second cam lever; and a cable operatively connected to the orthopedic device and operatively connected to the body portion; wherein rotation of the screw gear causes translation of the screw drive.

18 Claims, 11 Drawing Sheets

(51) Int. Cl.
     A61B 17/68      (2006.01)
     A61B 90/00      (2016.01)

(56) References Cited

U.S. PATENT DOCUMENTS

| | | | |
|---|---|---|---|
| 2010/0042106 A1* | 2/2010 | Bryant | A61B 17/8869 606/103 |
| 2010/0318137 A1 | 12/2010 | Stucki et al. | |
| 2011/0112537 A1 | 5/2011 | Bernstein et al. | |
| 2012/0165880 A1 | 6/2012 | Levy et al. | |

OTHER PUBLICATIONS

Written Opinion related to International App. No. PCT/US2014/068952.

European Search report in European patent application No. 14868468.1 dated Jul. 28, 2017, 12 pgs.

* cited by examiner

┌─────────────────────────────────────────────────────────────┐
    │ Providing a screw drive; a screw gear; at least one          │
    │ compression spring; a body portion comprising a first cam    │
    │ lever and a second cam lever, wherein a first end of a cable │ 1102
    │ may be engaged between the first cam lever and the body      │
    │ portion, and wherein a second end of the cable may be        │
    │ engaged between the second cam lever and the body            │
    │ portion; and providing a hand ratchet operatively connected  │
    │ to the screw gear.                                           │
    └─────────────────────────────────────────────────────────────┘
                                   ↓
    ┌─────────────────────────────────────────────────────────────┐
    │ Engaging the first end of the cable between the first cam    │ 1104
    │ lever and the body portion.                                  │
    └─────────────────────────────────────────────────────────────┘
                                   ↓
    ┌─────────────────────────────────────────────────────────────┐
    │ Engaging the second end of the cable between the second      │ 1106
    │ cam lever and the body portion.                              │
    └─────────────────────────────────────────────────────────────┘
                                   ↓
    ┌─────────────────────────────────────────────────────────────┐
    │ Rotating the hand ratchet to cause a rotation of the screw   │ 1108
    │ gear.                                                        │
    └─────────────────────────────────────────────────────────────┘
                                   ↓
    ┌─────────────────────────────────────────────────────────────┐
    │ Rotating the screw gear to cause a translation of the screw  │ 1110
    │ drive.                                                       │
    └─────────────────────────────────────────────────────────────┘
                                   ↓
    ┌─────────────────────────────────────────────────────────────┐
    │ Translating the screw drive to cause a compression of the at │ 1112
    │ least one compression spring.                                │
    └─────────────────────────────────────────────────────────────┘
                                   ↓
    ┌─────────────────────────────────────────────────────────────┐
    │ Compressing the at least one compression spring to cause a   │ 1114
    │ force to be applied to the body portion.                     │
    └─────────────────────────────────────────────────────────────┘
                                   ↓
    ┌─────────────────────────────────────────────────────────────┐
    │ Applying a force to the body portion to cause a tension in   │ 1116
    │ the cable.                                                   │
    └─────────────────────────────────────────────────────────────┘
```

FIG. 11

DEVICE FOR TENSIONING APPARATUS FOR FUSION, STABILIZATION, AND/OR FIXATION OF BONES

CROSS-REFERENCE TO RELATED APPLICATIONS

This application claims priority from U.S. Provisional Patent Application No. 61/912,540, filed on Dec. 5, 2013, and U.S. Provisional Patent Application No. 61/925,644, filed on Jan. 9, 2014, each of which is incorporated by reference herein in its entirety.

BACKGROUND

The implantation, use, and tensioning of orthopedic implanted devices for fusion, stabilization, and fixation of joints, fractures, and other fusions may involve various complicated processes and components. One such process may be the tensioning of an orthopedic implanted device, such as a nail, to compress, to a desired value, a joint, fracture, or other fusion falling within the length of the orthopedic implanted device. The present application appreciates that tensioning an orthopedic implanted device to compress a joint, fracture, or other fusion may be a challenging endeavor.

SUMMARY

In one embodiment, a tensioning device is provided. The tensioning device may include a screw drive. The tensioning device may also include a screw gear. The tensioning device may further include at least one compression spring. The tensioning device may include a body portion having a first cam lever and a second cam lever. A first end of a cable may be engaged between the first cam lever and the body portion. A second end of the cable may be engaged between the second cam lever and the body portion. A hand ratchet may be operatively connected to the screw gear. Rotation of the hand ratchet may cause rotation of the screw gear. Rotation of the screw gear may cause translation of the screw drive. Translation of the screw drive may cause compression of the at least one compression spring. Compression of the at least one compression spring may cause a force to be applied to the body portion. The force applied to the body portion may cause a tension in the cable.

In another embodiment, a device for tensioning an orthopedic device is provided, the device comprising: a screw drive; a screw gear; a body portion comprising a first cam lever and a second cam lever; and a cable operatively connected to the orthopedic device and operatively connected to the body portion; wherein rotation of the screw gear causes translation of the screw drive.

In another embodiment, a device for tensioning an orthopedic device is provided, the device comprising: a screw drive; a screw gear; a body portion comprising a first cam lever and a second cam lever; and a compression spring oriented between the screw drive and the body portion; wherein rotation of the screw gear causes translation of the screw drive.

In one embodiment, a method for using a tensioning device is provided. The method may include providing a screw drive. The method may also include providing a screw gear. The method may further include providing at least one compression spring. The method may include providing a body portion. The body portion may include a first cam lever and a second cam lever. A first end of a cable may be engaged between the first cam lever and the body portion. A second end of the cable may be engaged between the second cam lever and the body portion. The method may also include providing a hand ratchet operatively connected to the screw gear. The method may further include engaging the first end of the cable between the first cam lever and the body portion. The method may include engaging the second end of the cable between the second cam lever and the body portion. The method may also include rotating the hand ratchet to cause a rotation of the screw gear. The method may further include rotating the screw gear to cause a translation of the screw drive. The method may include translating the screw drive to cause a compression of the at least one compression spring. The method may also include compressing the at least one compression spring to cause a force to be applied to the body portion. The method may further include applying a force to the body portion to cause a tension in the cable.

In another embodiment, a method for using a tensioning device to provide tension in an orthopedic device is provided, the method comprising: providing a screw drive; providing a screw gear; providing at least one compression spring; providing a body portion comprising a first cam lever and a second cam lever, wherein a first end of a cable is engageable between the first cam lever and the body portion, and wherein a second end of the cable is engageable between the second cam lever and the body portion; and providing a hand ratchet operatively connected to the screw gear; engaging the first end of the cable between the first cam lever and the body portion; engaging the second end of the cable between the second cam lever and the body portion; rotating the hand ratchet to cause a rotation of the screw gear; rotating the screw gear to cause a translation of the screw drive; translating the screw drive to cause a compression of the at least one compression spring; compressing the at least one compression spring to cause a force to be applied to the body portion; and applying a force to the body portion to cause a tension in the cable.

BRIEF DESCRIPTION OF THE DRAWINGS

The accompanying figures, which are incorporated in and constitute a part of the specification, illustrate various example configurations and systems, and are used merely to illustrate various example embodiments. In the figures, like elements bear like reference numerals.

DETAILED DESCRIPTION

Patients may suffer from a fracture, joint problem, or other situation in which one or more bones may be in need of fusion. An orthopedic device may be implanted to span the fracture, joint, or other fusion site and facilitate compression and fusion of the bone. When installing an orthopedic device, such as a nail through a patient's ankle (e.g., through the calcaneus and talus, and into the tibia), a surgeon may install the nail from the patient's heel. The orthopedic device may span across the joint, fracture, or other fusion.

Providing compression to a joint, fracture, or other site to be fused may improve fusion of bone in that site. However, achieving adequate and/or desired levels of compression can be very difficult. Accurate application of a specific compression to a fusion site may be extremely beneficial to a surgeon installing an orthopedic device. Such application may be further beneficial if it can be replicated in other patients and adjusted and studied to determine desired levels of compression on a case by case basis.

The orthopedic device, such as a nail, may include a tensioning cable therein configured such that providing tension to the cable provides compression to the joint, fracture, or other fusion. To effect the tensioning of a cable in an orthopedic device, and thus compression across a joint, fracture, or other site to be used, a cable tensioning device may provide a tension to the cable by effectively pulling and providing a force to the proximal ends of the cable.

The orthopedic device may include at least one transverse circular or transverse oblong hole for accepting transverse bolts, e.g., to attach the calcaneus, talus, and/or tibia to the nail. For example, the at least one transverse circular or transverse oblong hole may comprise two holes, wherein the two may be on both a proximal side of the joint, fracture, or other fusion, as well as a distal side of the joint, fracture, or other fusion. A surgeon may fix a first transverse bolt through both a first transverse hole and a patient's calcaneus, talus, or the like. For example, the first transverse hole may be on the proximal side of the joint, fracture, or other fusion. A surgeon may also fix a second transverse bolt through both a second, oblong, transverse hole and a patient's tibia. For example, the second, oblong, transverse hole may be on the distal side of the joint, fracture, or other fusion. The order of fixation may vary. For example, in some embodiments the second transverse bolt may be fixed prior to the first transverse bolt.

In one example embodiment of an orthopedic device, such as a nail through a patient's ankle, a surgeon may desire to tension the orthopedic device. The desired tension may in turn provide compression across a joint, fracture, or other fusion in the ankle. The nail may include a cable configured to extend about a second transverse bolt through both a second, oblong transverse hole, and a patient's bone. The second transverse bolt may be oriented on the distal side of a joint, fracture, or other fusion in the ankle. The ends of the cable may extend from the orthopedic device at a proximal end. Tensioning the cable may provide a compression in the joint, fracture, or other fusion.

Figure 1:
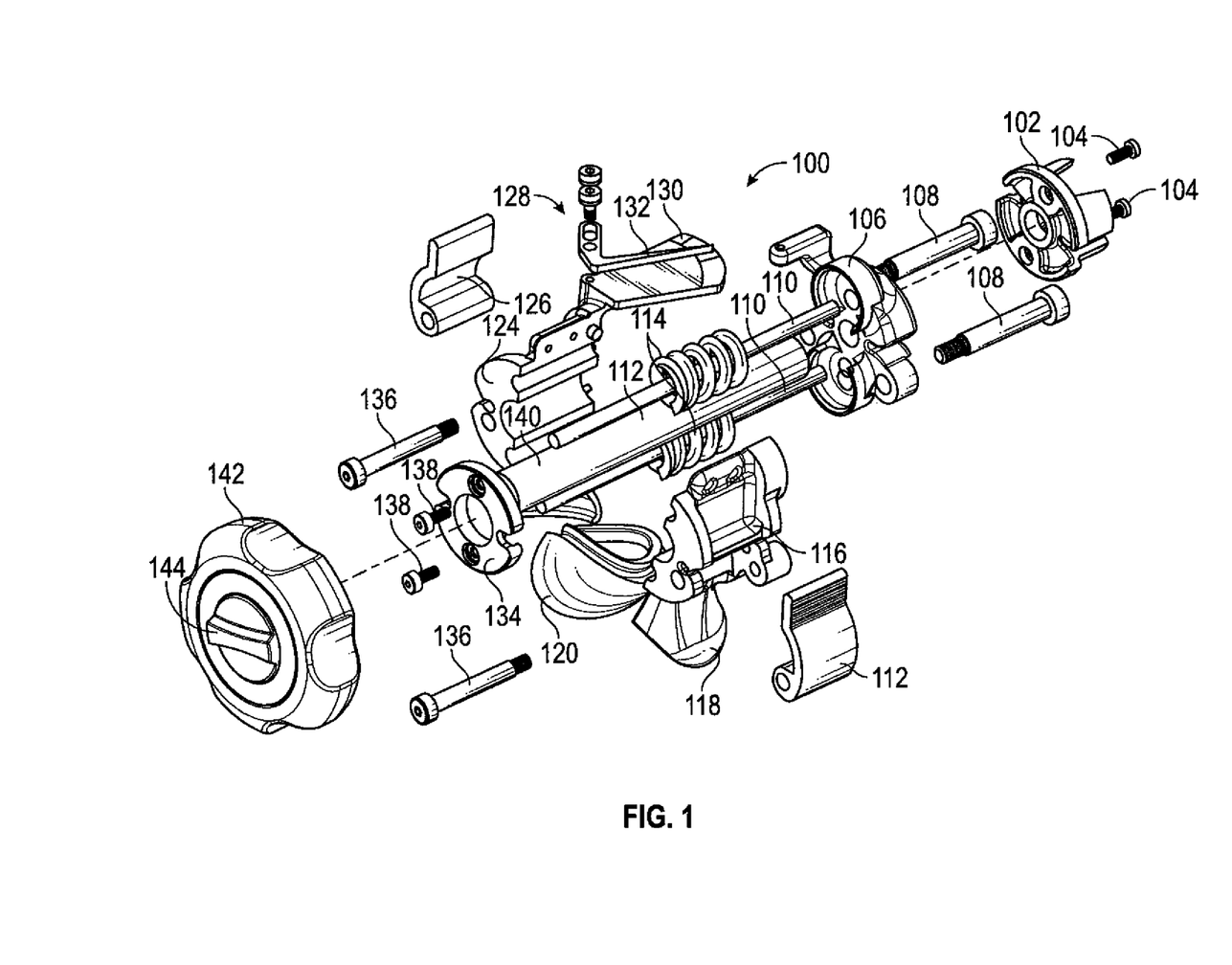
FIG. 1 is an exploded view of an example device for tensioning an apparatus for fusion, stabilization, and/or fixation of bones.

FIG. 1 is an exploded view of an example embodiment of a tensioning device 100. Tensioning device 100 may include a mount cap 102 and at least one mount cap bolt 104. Tensioning device 100 may include a screw drive 106 and at least one screw drive bolt 108. Tensioning device 100 may include at least one guide bar 110. Tensioning device 100 may also include a screw gear 112, and at least one compression spring 114.

Mount cap 102 may include a substantially cylindrical device configured to connected to a support device (not shown). Mount cap 102 may include at least one notch configured to align mount cap 102 in a desired orientation relative to a support device (not shown). Mount cap 102 may be configured to directly or operatively connect to at least one of a support device and an orthopedic device (not shown). Mount cap 102 may include at least one notch or finger configured to at least substantially mate with at least one notch or finger of a support device. Mount cap 102 may be configured to directly or operatively connect to a nail (not shown). Mount cap bolt 104 may directly or operatively connect to screw drive 106. Mount cap bolt 104 may be any of a variety of mechanical fasteners capable of selectively or permanently fixing mount cap 102 to screw drive 106.

Screw drive 106 may be operatively connected to screw gear 112. Screw drive 106 may be threadably engaged to screw gear 112, such that rotation of screw gear 112 may cause translation of screw drive 106. Screw gear 112 may include a threaded bolt. Screw gear 112 may include a threaded rod. Screw gear 112 may include male threads and screw drive 106 may include corresponding female threads. Screw gear 112 may include female threads and screw drive 106 may include corresponding male threads.

Tensioning device 100 may include a first body portion 116, comprising a first handle portion 118. First handle portion 118 may be operatively connected to a hand knob 120. First body portion 116 may be operatively connected to a first cam lever 122. Tensioning device 100 may include a second body portion 124. Second body portion 124 may include a second handle portion (not shown). The second handle portion may be operatively connected to hand knob 120. Second body portion 124 may be operatively connected to a second cam lever 126. First body portion 116 and second body portion 124 may be connected to one another to form a single body portion, and may be referred to as such herein.

First body portion 116 and second body portion 124 may be connected through any of a variety of mechanical fasteners, including at least one of a bolt, a screw, a rivet, a nail, an adhesive, a weld, a friction fit, a press fit, and the like. The single body portion may be formed from a single element, and may not include first body portion 116 and second body portion 124.

Screw drive 106 may be operatively connected to the single body portion by at least one screw drive bolt 108. Screw drive 106 may be directly connected to the single body portion by at least one screw drive bolt 108. At least one screw drive bolt 108 may permit screw drive 106 to slide or otherwise translate toward the single body portion from an initial position. At least one screw drive bolt 108 may be configured to restrain screw drive 106 from moving away from the single body portion farther than the initial position.

For example, screw drive 106 may include a head portion (not shown) configured to prevent screw drive 106 from extending away from the single body portion farther than an initial position. The head portion (not shown) may allow screw drive 106 to move toward the single body portion along at least one screw drive bolt 108. At least one screw drive bolt 108 may include a bolt head configured to at least partially engage screw drive 106 and keep it from moving away from the single body portion farther than the initial position. The bold head may be configured to at least partially engage the head portion of screw drive 106 and keep it from moving away from the single body portion farther than the initial position.

At least one compression spring 114 may be oriented between screw drive 106 and the single body portion. At least one of screw drive 106 and the single body portion may include a bearing portion configured to contact compression spring 114. The bearing portion may be at least partially recessed in screw drive 106 to ensure proper engagement between screw drive 106 and compression spring 114.

Screw drive 106 may be operatively connected to the single body portion via at least one guide bar 110. At least one compression spring 114 may extend about at least one guide bar 110. Each compression spring 114 may correspond to one guide bar 110. At least one guide bar 110 may extend from mount cap 102 to an end cap 134. At least one guide bar 110 may extend from mount cap 102, through screw drive 106, through compression spring 114, and through the single body portion to end cap 134.

Compression spring 114 may be configured to provide force against screw drive 106 and the single body portion. Screw drive 106 may translate along screw gear 112 and may cause compression of compression spring 114. Compression spring 114 may include a greater or lesser spring rate such that compression of compression spring 114 may cause compression spring 114 to provide greater or lesser force against screw drive 106 and the single body portion. Selection of compression spring 114, and its spring rate, may vary on a case by case basis depending upon the desired force to be provided by compression spring 114. Force applied by compression spring 114 may cause the single body portion to move away from mount cap 102 and provide tension to a cable (not shown).

First cam lever 122 and second cam lever 126 may be configured to pivot against first body portion 116 and second body portion 124, respectively. At least one of first cam lever 122 and second cam lever 126 may be configured to cause a cable (not shown) to be captured. The cable (not shown) may be captured between first cam lever 122 and first body portion 116, and second cam lever 126 and second body portion 124. The cable may be forcefully squeezed between first cam lever 122 and first body portion 116, and second cam lever 126 and second body portion 124, such that pivoting of first cam lever 122 and second cam lever 126 may selectively capture and release the cable (not shown). Actuating first cam lever 122 toward first body portion 116 may cause engagement of the cable, while actuating first cam lever 122 away from first body portion 116 may cause release of the cable. Actuating second cam lever 126 toward second body portion 124 may cause engagement of the cable, while actuating second cam lever 126 away from second body portion 124 may cause release of the cable. Tensioning device 100 may be assembled such that the cable (not shown) extending from an orthopedic device may be clamped between first body portion 116 and first cam lever 122 on a first end of the cable, and may be clamped between second body portion 124 and second cam lever 126 on a second end of the cable.

Tensioning device 100 may include a gauge 128. Gauge 128 may include a scale 130 and a needle 132. Gauge 128 may be configured to measure at least one of tension in a cable (not shown), compression across a joint, fracture, or other fusion site, and pressure in a joint, fracture, or other fusion site.

Tensioning device 100 may include end cap 134, at least one cam lever bolt 136, at least one end cap bolt 138. End cap 134 may be operatively or directly connected to the single body portion via at least one end cap bolt 138.

At least one cam lever bolt 136 may attach first cam lever 122 and second cam lever 126 to first body portion 116 and second body portion 124, respectively. First cam lever 122 and second cam lever 126 may be configured to pivot about at least one cam lever bolt 136.

Tensioning device 100 may include a driver device 140. Driver device 140 may be operatively connected to a hand ratchet 142. Driver device 140 may be operatively, or directly, connected to screw gear 112. Rotation of driver device 140 may cause rotation of screw gear 112. Hand ratchet 142 may be substituted with a handle that does not ratchet (not shown).

Hand ratchet 142 may include a substantially circular ratchet configured to be grasped and rotated by a user. Hand ratchet 142 may include a lever arm to provide leverage to a user rotating hand ratchet 142. Hand ratchet 142 may include a device configured to assist a user in rotating hand ratchet 142. The device may include, for example, any of a motor, an actuator, and the like.

Hand ratchet 142 may include a direction selector 144 configured to change a direction of force applied in hand ratchet 142, for example, clockwise versus counterclockwise. Rotating hand ratchet 142 in a first rotational direction, e.g., clockwise, may cause screw gear 112 to rotate in the first rotational direction and may cause screw drive 106 to translate in a first translation direction. Rotating hand ratchet 142 in a second rotational direction, e.g., counterclockwise, may cause screw gear 112 to rotate in the second rotational direction and may cause screw drive 106 to translate in a second translational direction.

Tensioning device 100 may be assembled such that screw drive 106 may be mated with screw gear 112. Rotation of screw gear 112 may result in translation of screw drive 106. Hand ratchet 142 may be operatively connected to screw gear 112. Rotation of hand ratchet 142 may result in rotation of screw gear 112. First body portion 116 and second body portion 124 may be connected to create a single body portion. The single body portion may be operatively connected to screw drive 106 by at least one compression spring 114.

In one example method, rotation of hand ratchet 142 may result in rotation of screw gear 112. Rotation of screw gear 112 may result in translation of screw drive 106 toward hand ratchet 142. Translation of screw drive 106 may cause force to be applied to at least one compression spring 114. At least one compression spring 114 may in turn cause the single body portion to translate toward hand ratchet 142. The cable (not shown) may be connected to the single body portion by first cam lever 122 and second cam lever 126. Translation of the single body portion and force applied to the single body portion may result in force being applied to the cable in the form of tension.

At least one compression spring 114 may be compressed by screw drive 106. Compression by screw drive 106 may be directly related to the force at least one compression spring 114 applies to the single body portion. For example, at least one compression spring 114 may have a spring rate. The spring rate may result in a specific force being applied by at least one compression spring 114 after compression by screw drive 106. A measure of force applied to the single body portion, and corresponding tension applied to the cable, may be indicated through a measure of compression of at least one compression spring 114. It is understood that force imparted by a compression spring is directly related to the distance that the compression spring is compressed.

At least one compression spring 114 may be eliminated. Screw drive 106 may be connected to the single body portion via any attachment means, for example a bolt, a rod, and the like. Translation of screw drive 106 may result in translation of the single body portion. Translation of screw drive 106 may result in force applied to the single body portion.

Figure 2:
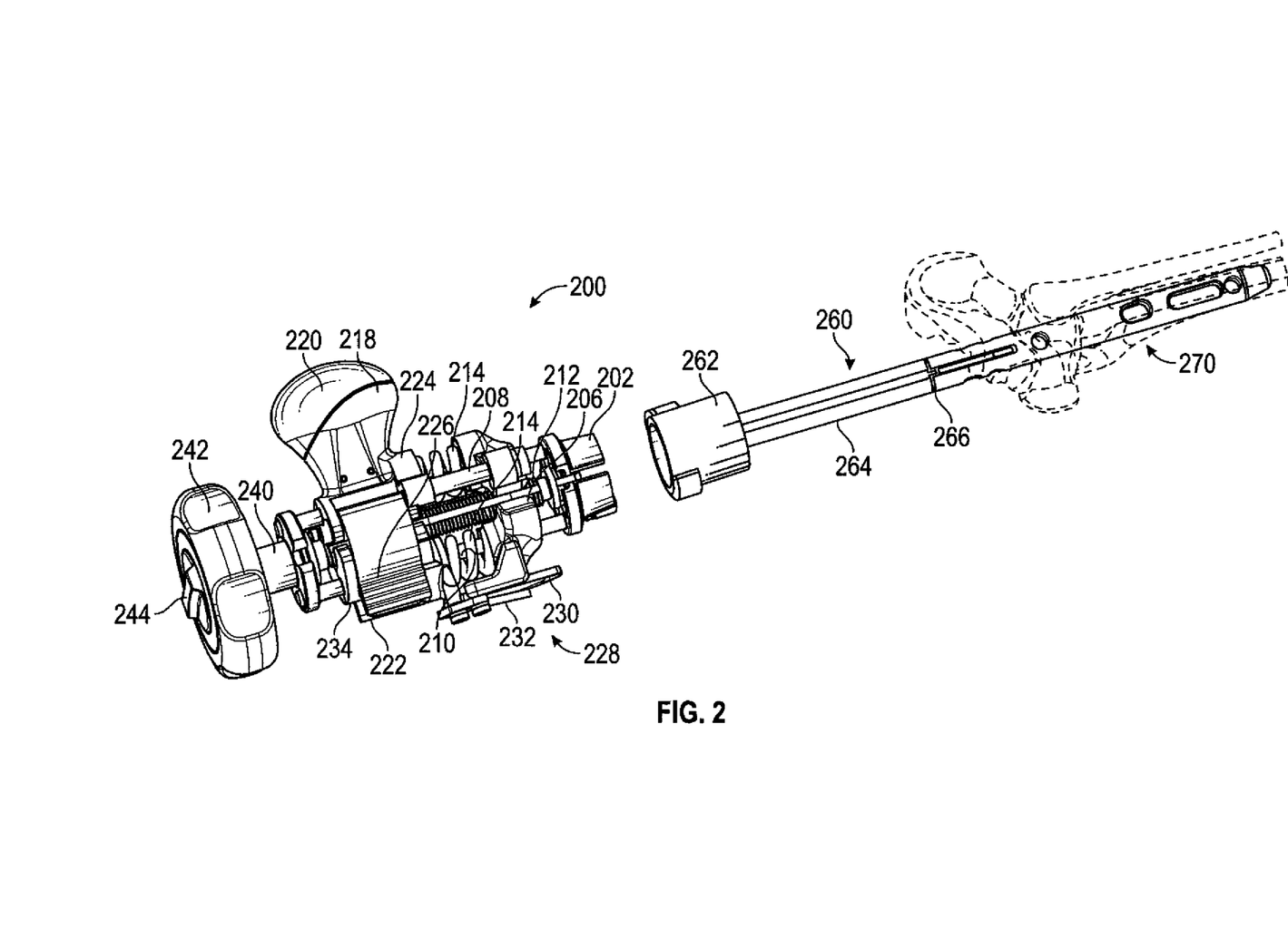
FIG. 2 is a perspective view of an example device 200 for tensioning an apparatus for fusion, stabilization, and/or fixation of bones, illustrated with a support device 260 and a nail 270.

FIG. 2 is a perspective view of an example embodiment of a tensioning device 200. Tensioning device 200 may include a mount cap 202. Tensioning device 200 may include a screw drive 206. Tensioning device 200 may include at least one screw drive bolt 208. Tensioning device 200 may include at least one guide bar 210. Tensioning device 200 may include a screw gear 212. Tensioning device 200 may include at least one compression spring 214.

Tensioning device 200 may include a second body portion 224. Second body portion 224 may include a second handle portion 218 and a hand knob 220. Tensioning device 200 may include a first body portion (not shown) and a first handle portion (not shown). First body portion (not shown) and second body portion 224 may be connected, removably or integrally. First body portion (not shown) and second body portion 224 may be referred to herein as a single body portion. The single body portion may be formed from a single element and may not include the first body portion (not shown) and second body portion 224.

Hand knob 220 may be configured to allow a user to grasp tensioning device 200. Hand knob 220 may be oriented or configured in any of a number of positions, directions, shapes, locations, and the like. Hand knob 220 may be oriented substantially perpendicularly to the longitudinal axis of screw gear 212. Hand knob 220 may be oriented at an angle relative to the longitudinal axis of screw gear 212. Tensioning device 200 may include a plurality of hand knobs 220. Tensioning device 200 may include a first cam lever 222 and a second cam lever 226.

Tensioning device 200 may include a gauge 228. Gauge 228 may include a scale 230 and a needle 232.

Tensioning device 200 may include, for example, an end cap 234, a hand ratchet 242, and a direction selector 244. Tensioning device 200 may include a driver device 240. Driver device 240 may operatively connect hand ratchet 242 to screw gear 212.

Mount cap 202 may be configured to attach tensioning device 200 to a support device 260, for example, via a support mounting portion 262. Support mounting portion 262 and mount cap 202 may mount such that support mounting portion 262 and mount cap 202 selectively do not move relative to one another in at least one of a rotational, axial, and transverse direction. Mount cap 202 may be engageable with support device 260, which may be engageable with an orthopedic device, such as nail 270.

Support device 260 may additionally include an elongated shaft portion 264 and a nail mounting portion 266. Nail mounting portion 266 may be configured to mount support device 260 to an orthopedic device, such as nail 270. Tensioning device 200, support device 260, and nail 270 may be connected to one another in a substantially linear fashion. A cable (not shown) may extend from nail 270, along the interior, exterior, or portions of both, of support device 260. The cable (not shown) may extend from nail 270 to tensioning device 200. The cable may be selectively fixed to tensioning device 200 via first cam lever 222 and second cam lever 226. The cable (not shown) may engage with a first body portion (not shown) and second body portion 224, respectively.

Figure 3:
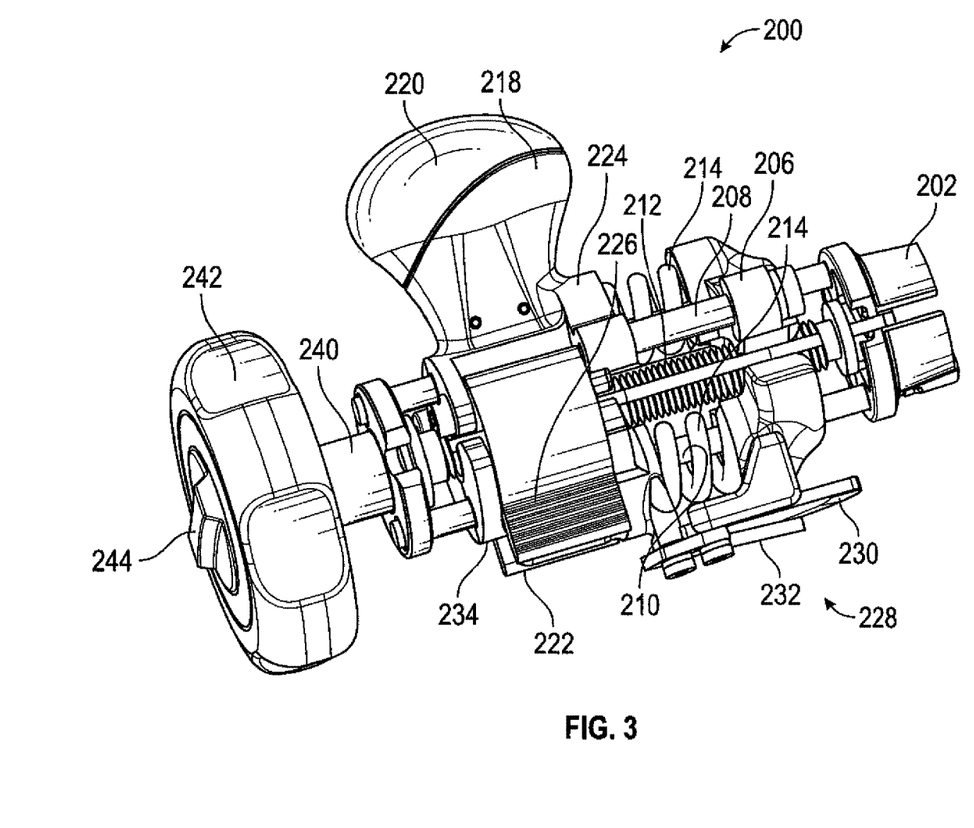
FIG. 3 is a perspective view of an example device for tensioning an apparatus for fusion, stabilization, and/or fixation of bones.

FIG. 3 is a perspective view of an example embodiment of tensioning device 200. FIG. 3 focuses specifically on tensioning device 200. Tensioning device 200 may include mount cap 202. Tensioning device 200 may include screw drive 206. Tensioning device 200 may include at least one screw drive bolt 208. Tensioning device 200 may include at least one guide bar 210. Tensioning device 200 may include screw gear 212. Tensioning device 200 may include at least one compression spring 214.

Figure 4:
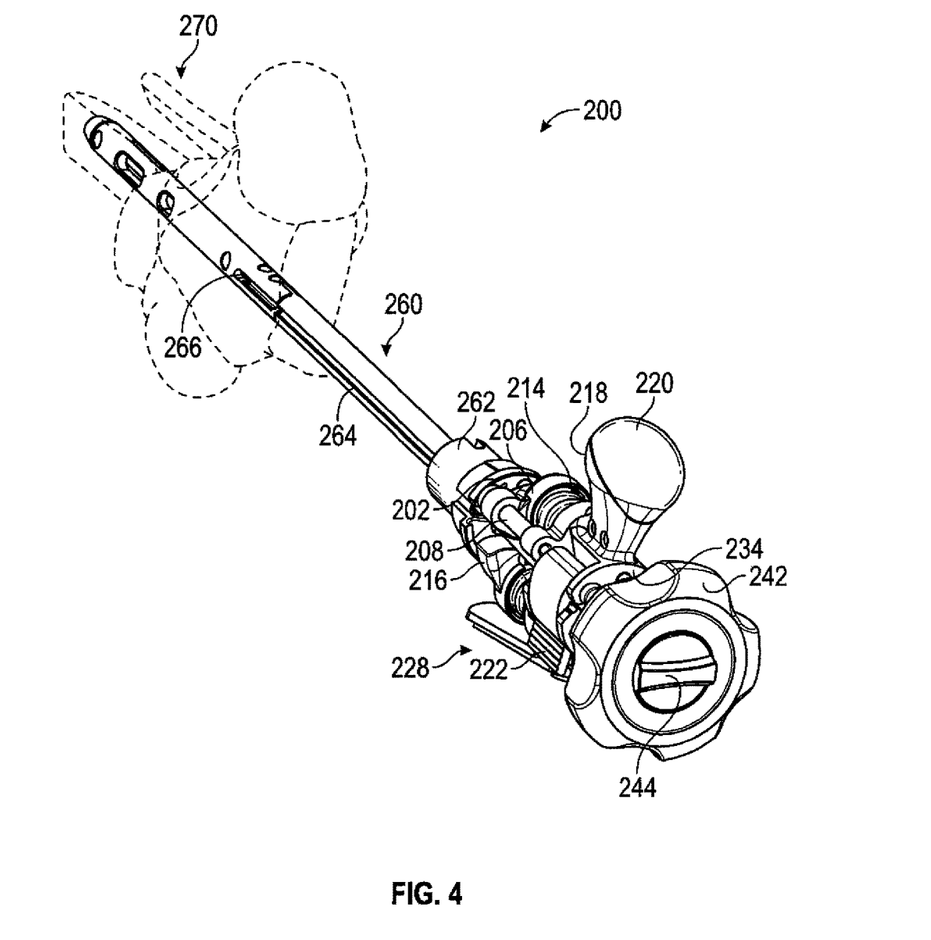
FIG. 4 is a perspective view of an example device 200 for tensioning an apparatus for fusion, stabilization, and/or fixation of bones, illustrated with a support device 260 and a nail 270.

FIG. 4 is a perspective view of an example embodiment of tensioning device 200. As illustrated, tensioning device 200 may include a first body portion 216.

Figure 5:
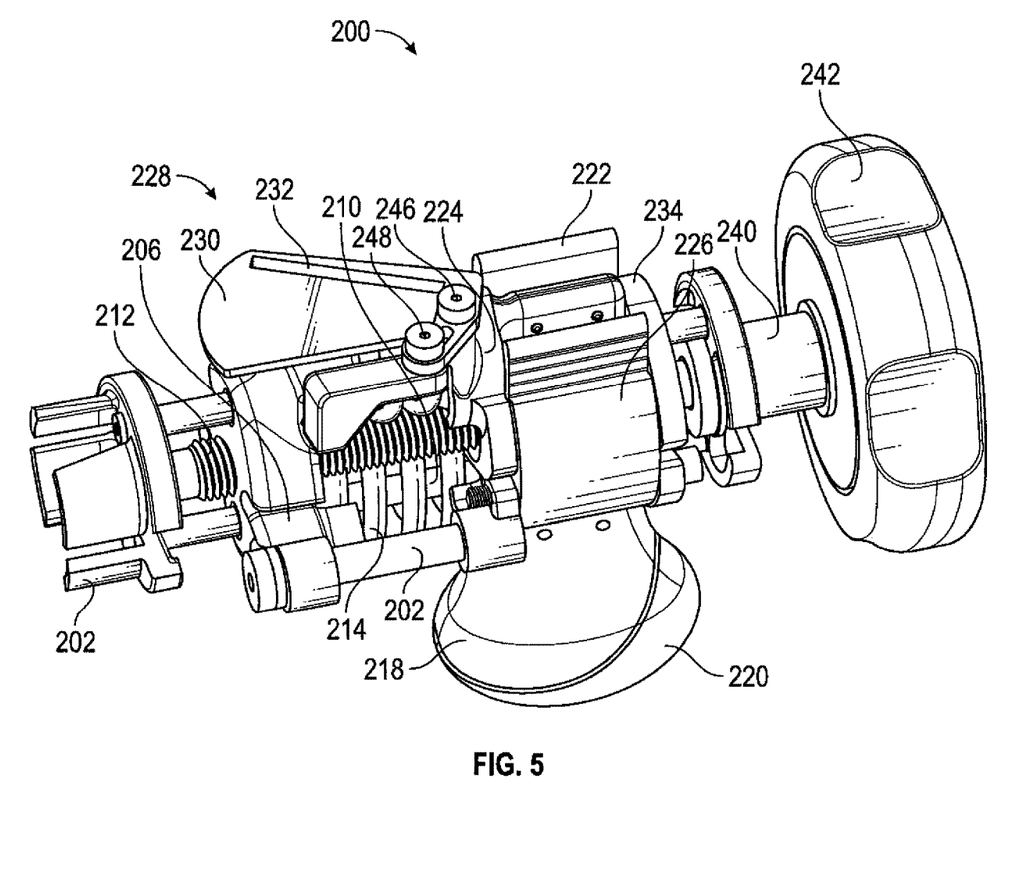
FIG. 5 is a perspective view of an example device for tensioning an apparatus for fusion, stabilization, and/or fixation of bones.

FIG. 5 is a perspective view of an example embodiment of tensioning device 200. As illustrated in FIG. 5, gauge 228 may include a scale 230 and a needle 232. Needle 232 may be pivotably attached to scale 230 via a pivot screw 246. Pivot screw 246 may include any of a variety of mechanical fasteners capable of permitting pivoting, including for example a screw, a bolt, a nail, a pin, a rivet, and the like. Needle 232 may be attached to screw drive 206 via a lever screw 248. Lever screw 248 may include any of a variety of mechanical fasteners, including for example a screw, a bolt, a nail, a pin, a rivet, and the like. Screw drive 206 may translate toward and away from ratchet handle 242. Translation of screw drive 206 may cause lever screw 248 to move with screw drive 206. Lever screw 248 may cause needle 232 to pivot about pivot screw 246. As needle 232 pivots, it may rotate along scale 230. Translation of screw drive 206 may be monitored and translated to a measurement of force applied to the first body portion (not shown) and second body portion 224 (combined as a single body portion). Measurement of force applied to the single body portion may be used to determine tension in the cable (not shown). The tension measurement may be displayed and identified by scale 230 and needle 232's position relative to scale 230. Scale 230 may indicate at least one of: tension in the cable; compression across a joint, fracture, or other fusion site; pressure across a joint, fracture, or other fusion site; and the like.

Screw drive 206 may translate toward hand ratchet 242 and needle 232 may move counter-clockwise relative to scale 230. Screw drive 206 may translate away from hand ratchet 242 and needle 232 may move clockwise relative to scale 230.

Figure 6:
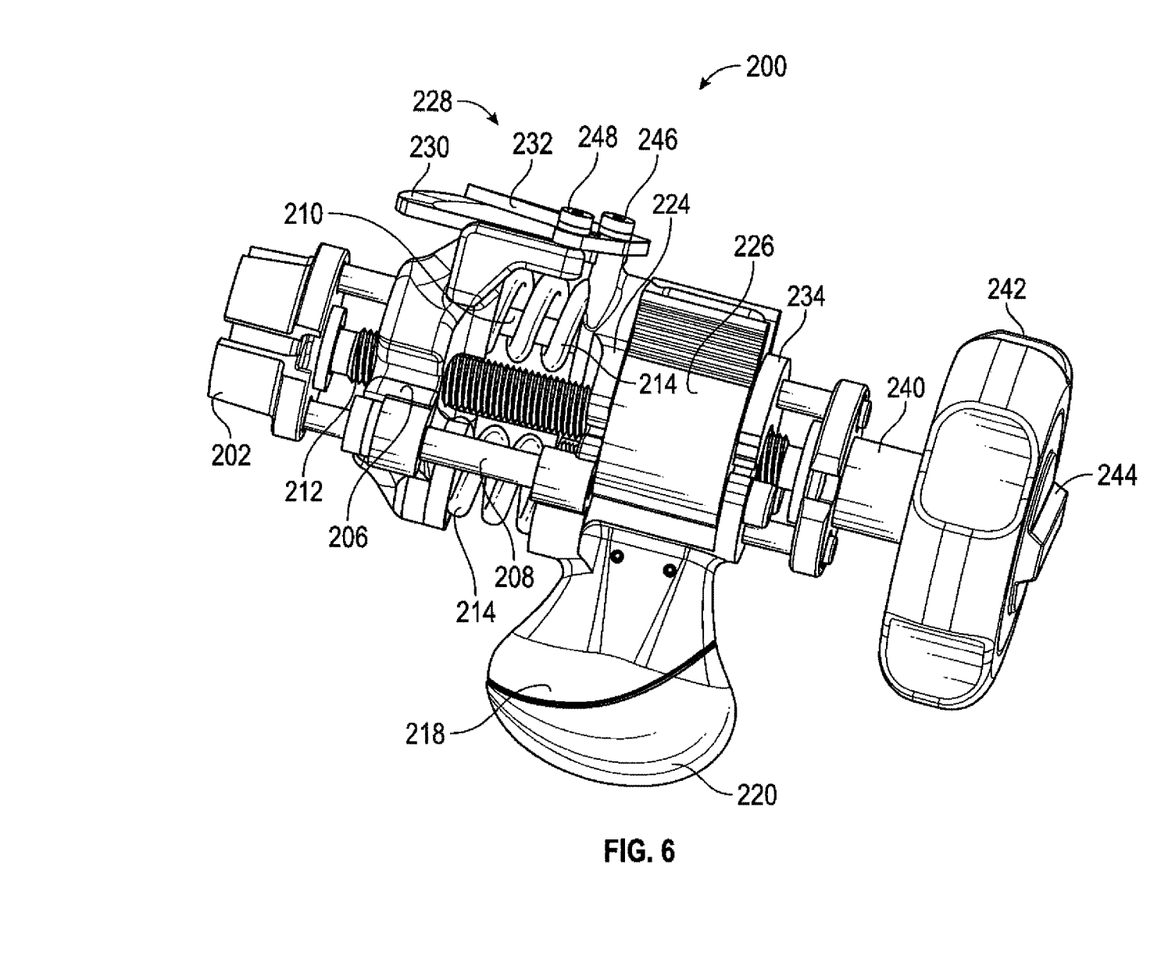
FIG. 6 is a perspective view of an example device for tensioning an apparatus for fusion, stabilization, and/or fixation of bones.

FIG. 6 is a perspective view of an example embodiment of tensioning device 200. Tensioning device 200 may include mount cap 202. Tensioning device 200 may include screw drive 206. Tensioning device 200 may include at least one screw drive bolt 208. Tensioning device 200 may include at least one guide bar 210. Tensioning device 200 may include screw gear 212. Tensioning device 200 may include at least one compression spring 214.

Figure 7:
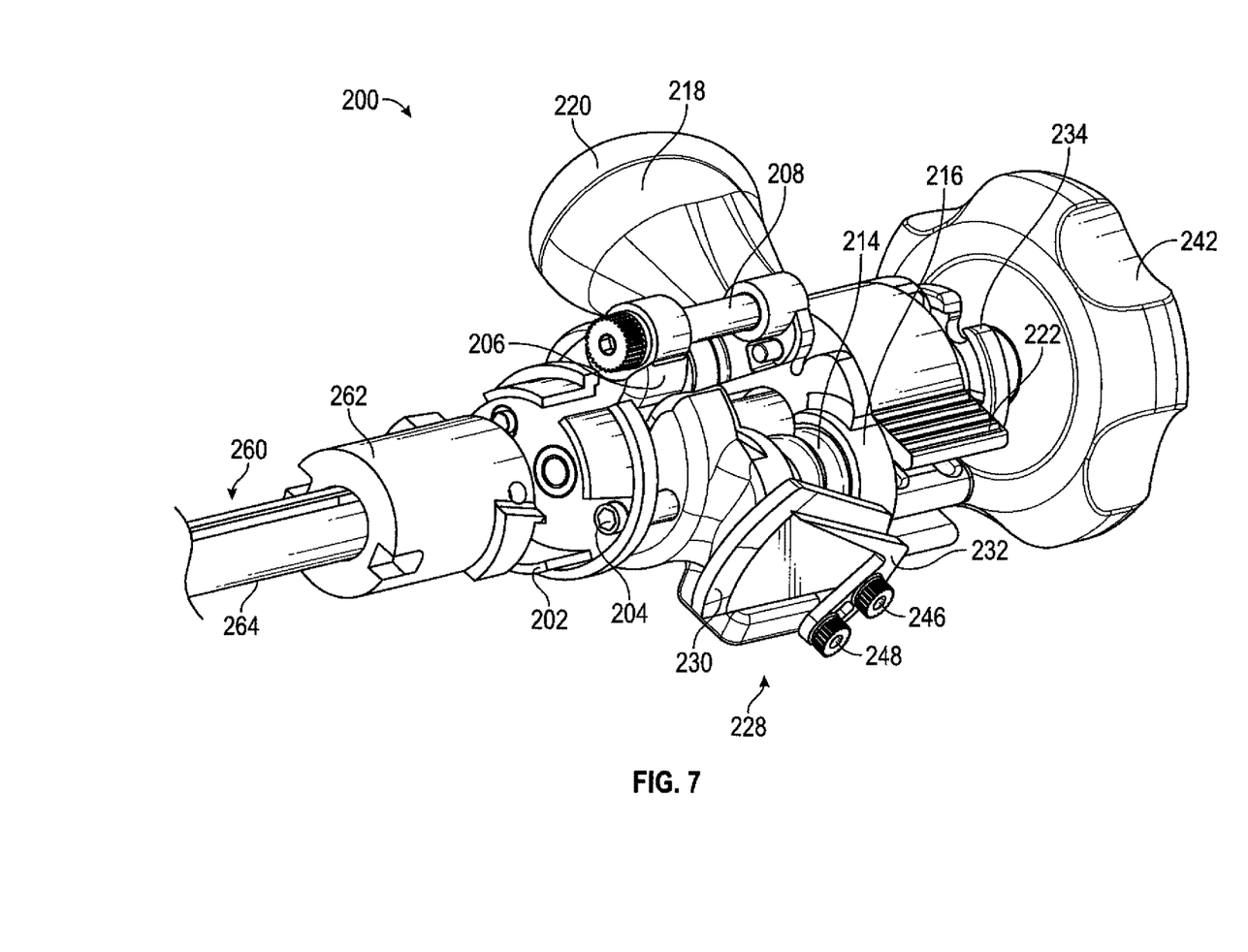
FIG. 7 is a perspective view of an example device for tensioning an apparatus for fusion, stabilization, and/or fixation of bones.

FIG. 7 is a perspective view of an example embodiment of tensioning device 200. Tensioning device 200 may include mount cap 202. Tensioning device 200 may include screw drive 206. Tensioning device 200 may include at least one screw drive bolt 208. Tensioning device 200 may include at least one compression spring 214.

Figure 8:
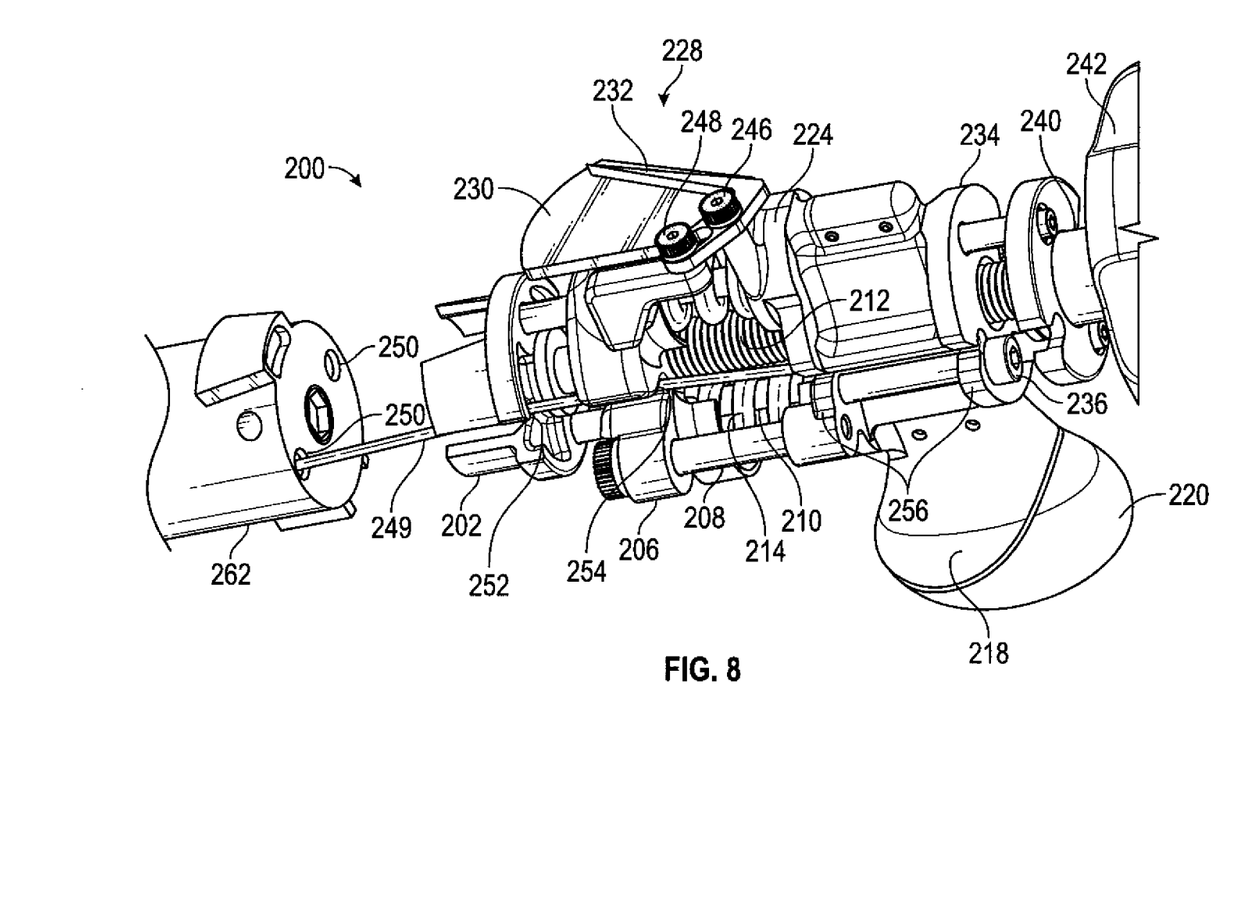
FIG. 8 is a perspective view of an example device for tensioning an apparatus for fusion, stabilization, and/or fixation of bones.

FIG. 8 is a perspective view of an example embodiment of tensioning device 200. As illustrated in FIG. 8, a cable 249 may extend through apertures 250 in support mounting portion 262. Tensioning device 200 may include at least one slot 252, 254, or 256 for routing of cable 249. Tensioning device 200 may include any of a variety of slots, apertures, grooves, and the like configured for routing and passage of cable 249.

First cam lever 222 and second cam lever 226 are removed in FIG. 8 to provide a view of slots 256. Cable 249 may extend through slots 256. A cam lever, such as second cam lever 226, may be rotated about a cam lever screw 236 and may contact cable 249 in a high pressure engagement. Cable 249 may be held by friction between second body portion 224 and second cam lever 226 and within slots 256. Cable 249 may be held by friction between first body portion 116 and first cam lever 222 in the same manner.

Figure 9:
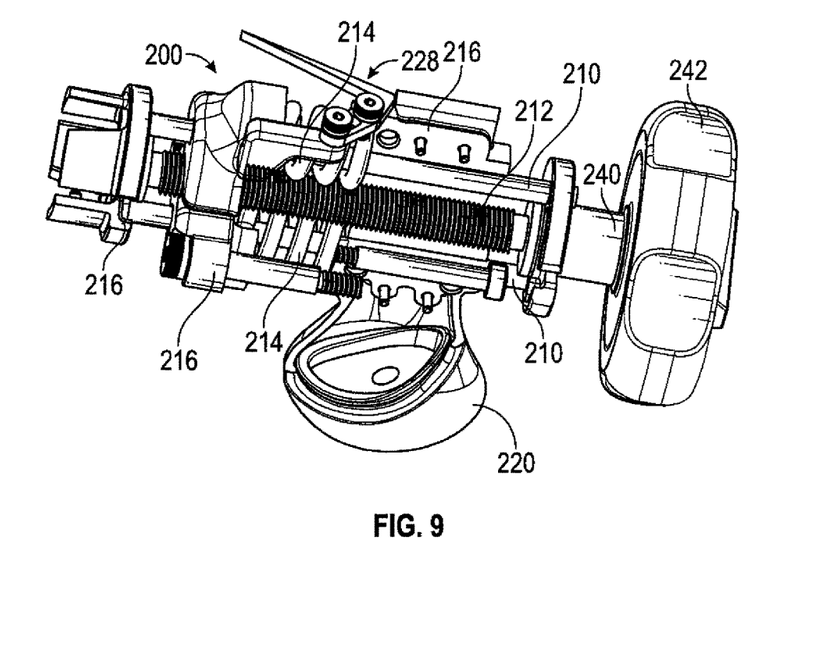
FIG. 9 is a perspective view of an example device for tensioning an apparatus for fusion, stabilization, and/or fixation of bones.

FIG. 9 is a perspective view of an example embodiment of tensioning device 200. In FIG. 9, second body portion 224 is removed to provide a view of screw gear 212 extending through an aperture between first body portion 216 and second body portion 224. The aperture between first body portion 216 and second body portion 224 may be larger than screw gear 212, such that screw gear 212 does not contact the aperture.

Figure 10:
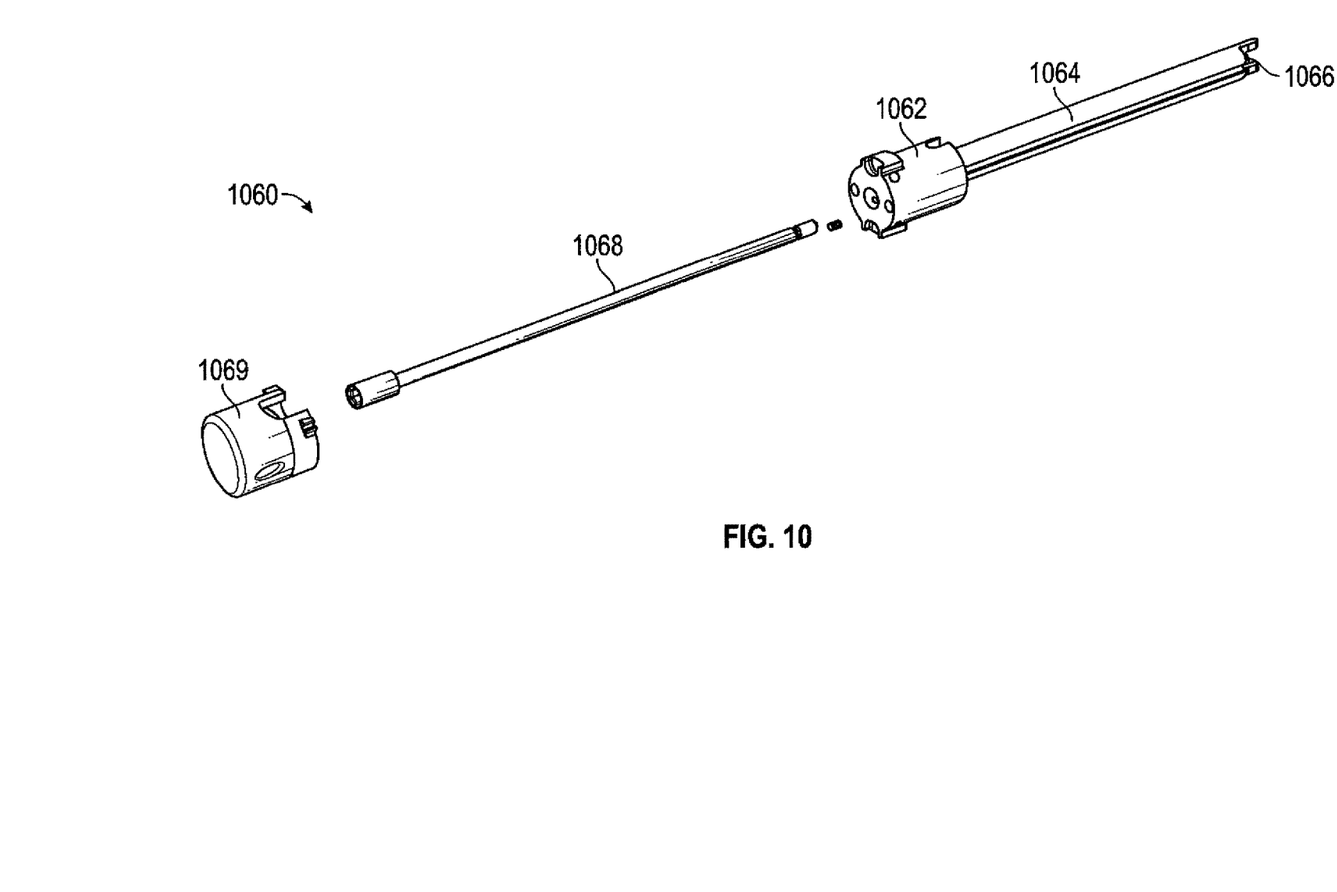
FIG. 10 is an exploded view of an example support device for use in tensioning an apparatus for fusion, stabilization, and/or fixation of bones.

FIG. 10 is an exploded view of an example support device 1060 for use in tensioning an apparatus for fusion, stabilization, and/or fixation of bones. Support device 1060 may include a support mounting portion 1062 configured to selectively connect support device 1060 to a tensioning device (not shown). Support device 1060 may include an elongated shaft portion 1064 and a nail mounting portion 1066. Nail mounting portion 1066 may be configured to mount support device 1060 to an orthopedic device, such as a nail (not shown).

Nail mounting portion 1066 may include a portion configured to engage an orthopedic device. Nail mounting portion 1066 may include a portion configured to engage a nail. Nail mounting portion 1066 may be configured to engage an orthopedic device such that the support device 1060 and the orthopedic device may not move relative to one another in at least one of a rotational, axial, and transverse direction.

Support device 1060 may include a nail fastener 1068, which may extend through elongated shaft portion 1064 in a longitudinal bore (not shown). Nail fastener 1068 may include a head at one end configured to be engaged by a tool, such as a wrench, screw driver, nut driver, and the like. Nail fastener 1068 may include threads at another end, configured to thread into an orthopedic device, such as a nail (not shown). Nail fastener 1068 may selectively attach support device 1060 to the orthopedic device. Nail fastener 1068 may be configured to restrict axial movement of support device 1060 relative to an orthopedic device.

Support device 1060 may include a hammer cap 1069. Hammer cap 1069 may be placed upon support mounting portion 1062 during installation of an orthopedic device, such as a nail. Support device 1060 may be used to drive an orthopedic device, such as a nail, into place, by a user striking hammer cap 1069 with a mallet or other device. Hammer cap 1069 may be removed prior to attaching a tensioning device (not shown) to support device 1060 via support mounting portion 1062.

Tensioning devices 100 and 200, and support devices 260 and 1060 may be used with any of a variety of orthopedic implant devices having a cable used to tension the implant and cause a compression in the joint, fracture, or other fusion.

Tensioning devices 100 and 200, and support devices 260 and 1060 may include any of a variety of materials, including for example a metal, an alloy, a polymer, a composite, and the like. At least one of tensioning devices 100 and 200, and support devices 260 and 1060 may include a stainless steel, e.g., a surgical stainless steel. At least one of tensioning devices 100 and 200, and support devices 260 and 1060 may include materials configured to be sterilized and used in a hospital and/or surgical environment.

Figure 11:
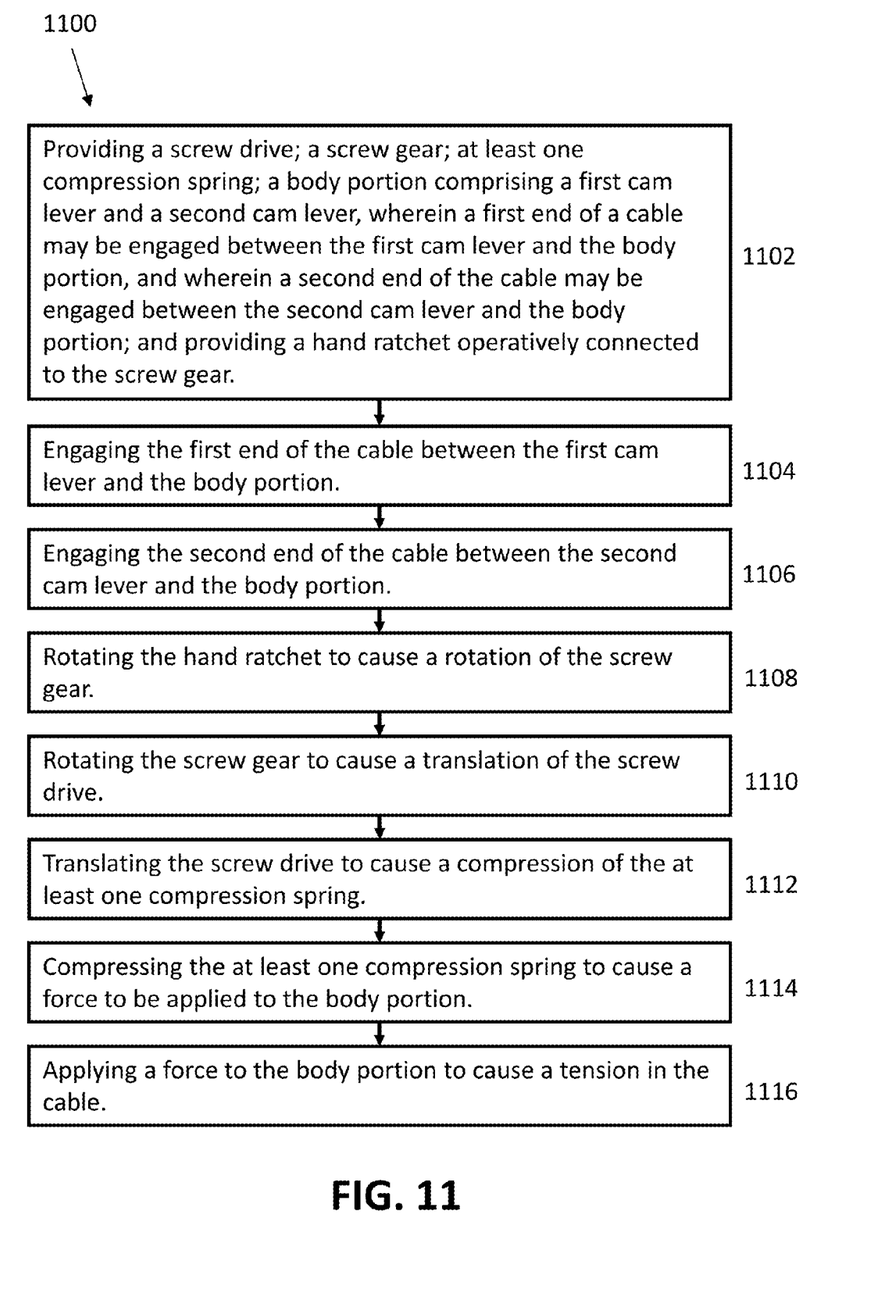
FIG. 11 is a flowchart of an example method for using a device for tensioning an apparatus for fusion, stabilization, and/or fixation of bones.

FIG. 11 is a flowchart illustrating an example method 1100 of using a tensioning device. Method 1100 may include providing a screw drive. Method 1100 may include providing a screw gear. Method 1100 also may include providing at least one compression spring. Method 1100 further may include providing a body portion comprising a first cam lever and a second cam lever. A first end of a cable may be engaged between the first cam lever and the body portion. A second end of the cable may be engaged between the second cam lever and the body portion. Method 1100 also may include providing a hand ratchet operatively connected to the screw gear. (Operation 1102). Method 1100 may include engaging the first end of the cable between the first cam lever and the body portion. (Operation 1104). Method 1100 may include engaging the second end of the cable between the second cam lever and the body portion. (Operation 1106). Method 1100 may include rotating the hand ratchet to cause a rotation of the screw gear. (Operation 1108). Method 1100 may include rotating the screw gear to cause a translation of the screw drive. (Operation 1110). Method 1100 may include translating the screw drive to cause a compression of the at least one compression spring. (Operation 1112). Method 1100 may include compressing the at least one compression spring to cause a force to be applied to the body portion. (Operation 1114). Method 1100 may include applying a force to the body portion to cause a tension in the cable. (Operation 1116).

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "substantially" is used in the specification or the claims, it is intended to take into consideration the degree of precision available or prudent in manufacturing. To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. As used in the specification and the claims, the singular forms "a," "an," and "the" include the plural. Finally, where the term "about" is used in conjunction with a number, it is intended to include ±10% of the number. In other words, "about 10" may mean from 9 to 11.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The invention claimed is:

1. A device for tensioning an orthopedic device, comprising:
    a screw drive;
    a body portion including first and second cam levers respectively configured to capture first and second ends of a cable simultaneously in conditions stationary relative to the body portion;
    a spring engaged between the screw drive and the body portion; and
    a screw gear engaged with the screw drive to translate the screw drive relative to the body portion to stress the spring, and thereby to apply a spring force urging the body portion and the captured ends of the cable distally away from the orthopedic device.

2. The device of claim 1, wherein the spring is a compression spring.

3. The device of claim 2, wherein translation of the screw drive causes compression of the compression spring.

4. The device of claim 3, wherein compression of the compression spring causes a force to be applied to the body portion.

5. The device of claim 1, further comprising a hand ratchet operatively connected to the screw gear.

6. The device of claim 1, further comprising a mount cap, wherein the mount cap is engageable with a support device, and wherein the support device is engageable with the orthopedic device.

7. The device of claim 1, further comprising a spring pressure gauge including a scale and a needle.

8. The device of claim 1, wherein the screw gear is engaged with the screw drive to translate the screw drive toward the body portion to compress the spring between the screw drive and the body portion, and thereby to apply a spring force urging the body portion and the captured ends of the cable away from the screw drive.

9. The device of claim 1, wherein the screw gear is engaged with the screw drive to translate the screw drive distally relative to the body portion to stress the spring between the screw drive and the body portion, and thereby to apply a spring force urging the body portion and the captured ends of the cable distally away from the screw drive.

10. The device of claim 8, further comprising a guide bar supporting the body portion and the screw drive for translation relative to one another along the guide bar.

11. The device of claim 9, wherein the spring is a coil spring received over the guide bar between the body portion and the screw drive.

12. A tensioning device for use with a cable extending about a transverse bolt in an orthopedic device, with opposite ends of the cable arranged distally relative to the orthopedic device, the tensioning device comprising:
    a screw drive;
    a body portion located distally of the screw drive, wherein the body portion is configured to capture the opposite ends of the cable simultaneously in conditions stationary relative to the body portion;
    a guide structure supporting the screw drive and the body portion for translation relative to the orthopedic device, and for translation relative to one another;
    a spring engaged between the screw drive and the body portion; and
    a screw gear engaged with the screw drive to translate the screw drive along the guide structure distally toward the body portion to stress the spring, whereby the stressed spring applies a spring force urging the body portion distally along the guide structure to pull the captured opposite ends of the cable distally away from the orthopedic device.

13. The device of claim 12, wherein the screw gear is engaged with the screw drive to translate the screw drive along the guide structure distally toward the body portion to compress the spring between the screw drive and the body portion.

14. The device of claim 12, wherein the guide structure includes a pair of laterally adjacent guide bars supporting the body portion and the screw drive for translation relative to one another along the guide bars.

15. The device of claim 14, wherein the spring is one of a pair of coil springs received over the guide bars between the body portion and the screw drive.

16. The device of claim 14, wherein the body portion includes first and second cam levers configured to capture the opposite ends of the cable in the conditions stationary relative to the body portion.

17. The device of claim 16, wherein the first and second cam levers have distally adjacent locations on the body portion.

18. The device of claim 16, wherein the first and second cam levers are located on laterally opposite sides of the body portion.

* * * * *